United States Patent [19]
Devlin et al.

[11] Patent Number: 5,908,636
[45] Date of Patent: Jun. 1, 1999

[54] FILL MATERIAL FOR SOFT GELATIN PHARMACEUTICAL DOSAGE FORM CONTAINING AN ANTIFLATULENT

[75] Inventors: Brid T. Devlin, Conshohocken; Michael R. Hoy, Sellersville, both of Pa.

[73] Assignee: McNeil-PPC, Inc., Skillman, N.J.

[21] Appl. No.: 08/671,988

[22] Filed: Jun. 28, 1996

[51] Int. Cl.$^6$ ..................................................... A61K 9/48
[52] U.S. Cl. .................. 424/452; 424/78.01; 424/454; 424/455; 424/456; 514/772.3; 514/781
[58] Field of Search ................................ 424/451, 452, 424/454, 456, 455, 453, 78.01

[56] References Cited

U.S. PATENT DOCUMENTS

| | | | |
|---|---|---|---|
| 4,486,412 | 12/1984 | Shah et al. | 424/156 |
| 4,673,570 | 6/1987 | Soldati | 424/66 |
| 4,708,834 | 11/1987 | Cohen et al. | 264/4.3 |
| 4,906,478 | 3/1990 | Valentine et al. | 424/682 |
| 4,935,243 | 6/1990 | Borkan et al. | 424/441 |
| 5,071,643 | 12/1991 | Yu et al. | 514/570 |
| 5,073,384 | 12/1991 | Valentine et al. | 424/474 |
| 5,275,822 | 1/1994 | Valentine et al. | 424/489 |

FOREIGN PATENT DOCUMENTS

| | | |
|---|---|---|
| 0 122 463 | 10/1984 | European Pat. Off. . |
| 0 271 925 A2 | 6/1988 | European Pat. Off. . |
| 0 310 252 A1 | 4/1989 | European Pat. Off. . |
| 0 422 290 A1 | 4/1991 | European Pat. Off. . |
| 0 425 450 A2 | 5/1991 | European Pat. Off. . |
| 0 428 296 A2 | 5/1991 | European Pat. Off. . |
| 0 490 582 A1 | 6/1992 | European Pat. Off. . |
| 2 624 012 | 6/1989 | France . |
| 44 10 710 A1 | 10/1995 | Germany . |
| 203477 | 1/1991 | Hungary . |
| 91/07950 | 6/1991 | WIPO . |
| 92/05767 | 4/1992 | WIPO . |
| 93/09761 | 5/1993 | WIPO . |
| 93/10797 | 6/1993 | WIPO . |
| 93/11752 | 6/1993 | WIPO . |

OTHER PUBLICATIONS

A. Banga et al. "Incorporation of Simethicone into Syrupy or Clear Base Liquid Orals", Drug Dev. and Indust. Pharm.., Article 15 (5), 691–704 (1989).

Translation only of "1 Introduction" B. Lippold, Influence of Vehicle on Drug Action in Solution Type Methylnicotinate Ointments, Acta Pharma. Technol. 35 (3), 128–135 (1989).

*Primary Examiner*—Thurman K. Page
*Assistant Examiner*—James M. Spear
*Attorney, Agent, or Firm*—Bernard F. Plantz

[57] ABSTRACT

The present invention relates to a semi-solid fill material for a soft gelatin capsule containing a therapeutically effective amount of an antiflatulent. The semi-solid is sufficiently viscous so that it cannot be expelled readily at room temperature from the capsule with a syringe.

27 Claims, No Drawings

5,908,636

FILL MATERIAL FOR SOFT GELATIN PHARMACEUTICAL DOSAGE FORM CONTAINING AN ANTIFLATULENT

This invention is also related to commonly assigned U.S. patent application Ser. No. 08/366,945, filed Dec. 29, 1994 now abandoned, entitled "Soft Gelatin Pharmaceutical Dosage Form"; Ser. No. 08/366,271, filed Dec. 29, 1994 U.S. Pat. No. 5,660,859, entitled "Gelling Agent for Polyethylene Glycol"; Ser. No. 08/871,991, filed Jun. 28, 1996, entitled "Fill Material for Soft Gelatin Pharmaceutical Dosage Form"; and Ser. No. 08/671,979, filed Jun. 28, 1996, entitled "Multiphase Soft Gelatin Dosage Form," all of which are hereby incorporated by reference.

FIELD OF THE INVENTION

The present invention relates to a soft gelatin capsule filled with a semi-solid containing a therapeutically effective amount of an antiflatulent.

BACKGROUND OF THE INVENTION

In recent years soft gelatin or soft elastic gelatin capsules have become a popular dosage form for the oral delivery of therapeutic agents, especially over-the-counter pharmaceuticals. These capsules are typically filled with a liquid containing the active ingredient. Because of their soft, elastic character, some patients view these capsules as easier to swallow than conventional tablets or hard gelatin capsules. Since the dosage form is generally swallowed, it is not necessary to flavor or otherwise mask the often unpleasant taste of the pharmaceutical. Soft gelatin capsules are also preferred to bulk liquids because they are easier to transport and they avoid the need for the patient to measure a prescribed amount of the liquid before dosing.

The fill material used in a soft gelatin capsule generally contains a pharmaceutical dissolved or dispersed in a carrier that is compatible with the capsule wall. In addition to liquids, U.S. Pat. No. 4,935,243 to L. Borkan et al. suggests that the fill material may take the form of a semi-solid, solid, or gel. Conventional tablets or pellets containing an active ingredient are examples of solid fill materials that may be encapsulated within a soft gelatin capsule.

Semi-solid (dispersion) fill material are discussed in U.S. Pat. No. 4,486,412 to D. Shah et al. A fill material containing an orally-administered antacid salt that is dispersed in a water-free, liquid carrier containing a major proportion of one or more polyalkylene glycols and a minor proportion of a $C_2$–$C_5$ polyol, such as propylene glycol or glycerin. The carrier forms a stable dispersion of the antacid salt and coats the antacid particles, thereby rendering them nonreactive with the soft gelatin capsule wall. The dispersion may also contain a polysiloxane flatulence-relieving agent, such as simethicone, as an optional ingredients. Such optional ingredients comprise about 0–5% by weight of the total dispersion.

U.S. Pat. No. 4,708,834 to Cohen et al. suggests a controlled release pharmaceutical dosage form comprising a soft gelatin capsule that encloses a watersoluble or dispersible gelled polymer matrix. The fill material comprises an aqueous solution or dispersion of a polysaccharide gum, the pharmaceutical active and, optionally, an alcohol. The liquid fill is introduced into a soft gelatin capsule that contains a cationic gelling agent, which gels the liquid fill after it has been incorporated into the capsule shell. The alcohol used in the fill includes liquid polyethylene glycols, lower alkanols, $C_2$–$C_4$ polyols and mixtures thereof.

U.S. Pat. No. 5,071,643 to M. Yu et al. also discusses the use of polyethylene glycols (PEG) as a fill material in soft gelatin dosage forms. PEGs having an average molecular weight between 400–600 are preferred for liquid fills, between 800–10,000 for semi-solid fills and between 10,000–100,000 for solid fills.

*Remington's Pharmaceutical Sciences*, 18th ed, Chapter 83, pp. 1539–40 (1990), reports that gelling agents used to make gels for pharmaceutical and cosmetic products, include sodium alginate and triethanolamine.

PCT Publication No. WO 91/07950 describes a soft or two-piece hard gelatin capsule shell containing benzodiazepine dissolved or suspended in a gel. The gel contains by weight at least 63% of polyethylene glycol 600, at least 4% of polyethylene glycol 4000 or 6000, and at least 21% of polyethylene glycol 600–4000. This gel fill cannot be expelled with a syringe at ambient temperature and therefore avoids the reported abuse of liquid filled capsules by intravenous drug abusers.

Antiflatulents are typically incorporated into compressible tablets by mixing the oily-like substances, such as simethicone, with standard tableting excipients prior to tableting. U.S. Pat. No. 5,073,384 to Valentine et al. describes a composition suitable for tableting comprising simethicone and a water soluble, maltodextrin agglomerate. The resulting combinate is reported to be free flowing and possess defoaming activity.

Hungarian Patent No. 203,477, published Jan. 28, 1991, describes an antiflatulent, solid dispersion containing poly (dimethylsiloxane) as a dispersed phase in a water soluble carrier. The dispersion also contains a lattice-forming and/or a crosslinking, viscosity-increasing macromolecular auxiliary substance such as polyvinyl chloride, polyacrylic acid, or polyvinylpyrrolidone and/or inorganic solidifying agent, such as tricalcium phosphate, calcium sulfate hemihydrate or calcium hydrogen phosphate. Example 1 reports a solid mass containing 60 g of polyethylene glycol 6000, 15 g of polyvinyl chloride and 25 g of activated dimethicone (simethicone) that can be ground and filled into solid gelatin capsules or made into tablets.

French Patent Application No. 2,624,012, published Jun. 9, 1989, relates to a soft gelatin capsule containing a suspension or solution of chloral hydrate in a high viscosity inert vehicle. Suitable vehicles for use in the capsule include oily solvents of mineral or vegetable oil, such as olive oil, peanut oil, paraffin oil, vaseline oil or mixtures of several oils; a liquid silicone such as dimethicone or simethicone; a glycol polymer such as polyethylene glycol 600, 800 or 1200; and a glycol such as ethylene glycol, propylene glycol or glycerol.

Simethicone has been incorporated in syrup or clear base liquid oral formulations. A. Banga et al. in "Incorporation of Simethicone into Syrup or Clear Base Liquid Orals," *Drug Development and Industrial Pharmacy*, 15(5), pgs. 691–704 (1989) describes a variety of vehicles for simethicone, but reports the best results were obtained with neutralized CARBOPOL® (carboxypolymethylene) resins in combination with glycerin and propylene glycol.

A need exists for a semi-solid fill material containing an antiflatulent suitable for use in the production of soft gelatin capsules. The fill material should be sufficiently viscous so as to prevent it from being expelled from the capsule shell with a syringe to minimize the potential for product tampering. The fill material should also not affect the defoaming properties of the antiflatulent.

SUMMARY OF THE INVENTION

The present invention provides a semi-solid fill material for a soft gelatin capsule comprising a polyalkylene glycol and an antiflatulent. The semi-solid is sufficiently viscous so that it cannot be expelled at room temperature from the capsule with a syringe, preferably having an 16 gauge or smaller needle. In a further embodiment of the present invention, the fill material has a viscosity of about 10,000 to about 2,500,000 centipoise (cP). The semi-solid fill material does not have a deleterious effect on the defoaming activity of the antiflatulent, such as simethicone.

DETAILED DESCRIPTION OF THE PREFERRED EMBODIMENTS

The present invention relates to a semi-solid containing an antiflatulent for filling a soft gelatin capsule pharmaceutical dosage form. The semi-solid may also be used to fill a two-piece hard gelatin capsule. The viscosity of the semi-solid is also controlled so that it cannot be readily removed from the capsule with a syringe at room temperature. This feature helps to protect against possible intravenous abuse of the drug as well as product tampering.

As used in the present invention, a semi-solid is a system of at least two constituents consisting of a condensed mass enclosing and interpenetrated by a liquid. The semi-solid fill material is sufficiently viscous so that an appreciable amount, less than about 1, preferably less than about 0.5, gram, cannot be expelled at room temperature with a syringe having a 16 gauge or smaller needle. The semi-solid preferably has a viscosity at 25° C. of about 10,000 to about 2,500,000, preferably about 400,000 to about 2,000,000, centipoise (cP).

The semi-solid of the present invention contains a polyalkylene glycol. Suitable polyalkylene glycols include polyethylene glycol (PEG) having an average molecular weight of about 400 to about 20,000, preferably about 400 to about 3350. The semi-solid generally comprises by weight about 30 to about 70, preferably about 40 to about 60, percent of the polyalkylene glycol. Unless otherwise stated, the percentages recited herein are by weight of the total weight of the semi-solid fill material, i.e., both the semi-solid and the antiflatulent.

Blends of PEGs of varying molecular weights may also be used in the semi-solid fill material of the present invention. The blends will generally contain low molecular weight PEGs having an average molecular weight of about 600 or less mixed with high molecular weight PEGs having an average molecular weight of greater than about 600 to about 10,000 in amounts that produce a semi-solid. Preferably, such blends contain about 0.25 to about 5 percent of the low molecular weight PEG and about 45 to about 50 percent of the high molecular weight PEG.

In addition to the liquid polyalkylene glycol, the semi-solid may contain one or more auxiliary semi-solid forming agents in the amount shown (% by wt. of semi-solid):

| % | Component |
| --- | --- |
| 0.05–10 | Propylene Glycol |
| 0.05–15 | Plurol Stearic (polyglyceryl-6-distearate) |
| 0.05–10 | Peceol (glycerol oleate) |
| 0.05–5 | Hydroxypropyl Cellulose, NF (KLUCEL HF; 1,150,00 MW) |

The semi-solid may contain 0 to about 10 percent water.

The antiflatulent is present in the dosage form in a therapeutically effective amount, which is an amount that produces the desired therapeutic response upon oral administration, and can be readily determined by one skilled in the art. In determining such amounts, the particular compound being administered, the bio-availability characteristics of the compound, the dose regime, the age and weight of the patient, and other factors must be considered. Antiflatulents suitable for use in the invention include simethicone and dimethicone. Generally, the antiflatulent comprises about 30 to about 70, preferably about 40 to about 60, percent by weight of the total semi-solid fill material. The defoaming time of semi-solid fill material containing the antiflatulent is preferably less than about 15, preferable less than about 9, seconds.

Various other pharmaceutically acceptable excipients may be included in the semi-solid fill material, such as preservatives, e.g., methyl- or propylparaben, coloring agents, flavoring agents, lubricants, flow-enhancers, antioxidants, humectants (glycerin), surfactants, plasticizers, filling aids and other compounds, agents and components which produce an appealing final product.

In a preferred embodiment, a semi-solid fill for a soft gelatin capsule containing 547 mg/mL simethicone, comprises by weight about 40 to about 60 percent simethicone, about 1 to about 3 percent liquid polyethylene glycol having an average molecular weight of about 300 to about 400 and about 40 to about 60 percent solid polyethylene glycol having an average molecular weight of about 1450 to about 4600. This semi-solid preferably has a viscosity of about 900,000 to about 1,000,000 cp at 25° C., a defoam time of less than about 8 seconds (as measured by the USP method described below) and a syringeability of less than 0.5 gram (as measured by the method described below).

The fill material of the present invention may be used in commercially available soft gelatin capsules, such as those commercially available from R. P. Scherer or Banner Pharmacaps. Various sizes, shapes, and colors can be used to accommodate different levels of active ingredients. The walls of the capsules have a substantially translucent or clear appearance. When the fill material of the present invention is introduced into the capsule and forms a semi-solid, the resulting dosage form has a white opaque appearance, or colorants may be added to achieve any desired color.

The fill material is heated before it is loaded into the capsule because it is highly viscous at temperatures below 40° C. Air-filled soft gelatin capsules can be hand filled with a syringe. The hot liquid fill is loaded into a syringe. The needle on the syringe is used to puncture one end of the soft gelatin capsule so that the appropriate amount of fill material may be injected by hand. The capsule with fill material is allowed to cool.

The fill material may also be introduced into the soft gelatin capsule using encapsulation equipment known in the art, such as that described in U.S. Pat. No. 4,028,024 to Moreland, which is hereby incorporated by reference. As previously described with the hand-filling technique, the fill must be maintained at above about 40° C. during the filling operation so that it readily flows into the capsule. Therefore, the fill can be stored in a jacketed vessel and transported through a thermostatically controlled feeding tube to the encapsulation equipment.

Specific embodiments of the present invention are illustrated by way of the following examples. This invention is not confined to the specific limitations set forth in these examples, but rather to the scope of the appended claims. Unless otherwise stated, the percentages and ratios given below are by weight of the total composition.

Viscosity was measured in the following examples using a Rheometrics Fluids Spectrometer 8400 at 25° C. Using a 25 mm parallel plate and a constant strain of 10%, frequency sweeps were performed. Viscosity was recorded at a frequency of 1.0 radian per second.

Defoaming testing in the following examples was carried out using United States Pharmacopeia 23 rev. The National Formulary 18 ed. specifications and procedures. The foaming solution consisted of 1% octoxynal-9 and 0.0005% FD&C Blue #1 in water. The testing equipment comprised a weight action shaker with radius set at 13.3±0.4 cm (measured from center of shaft to center of bottle) An equivalent of 20 mg simethicone was transferred into a jar containing 100 ml foaming solution, previously heated to 37° C. The jar was capped and shaken at an arc of 10 degrees at a frequency of 300+30 strokes/minute for 10 seconds. The time taken for a portion of foam-free liquid to appear was recorded. The USP limit being NMT 15 seconds.

Syringeability testing was performed in the following examples to measure the ability to syringe each formulation within a controlled time period. This test was used as a gauge of tamper resistance. 10 cc syringes were used with 16 gauge needles, 1.5 inches in length. The syringe was placed in the formulation, the plunger was pulled up and held for 10 seconds. The weight of the fill material pulled into the syringe was recorded.

EXAMPLE 1

This Example discloses semi-solid fill materials of the present invention containing 547 mg/ml simethicone. The following samples were prepared:

|  | Amount (% w/w) | | | | |
| --- | --- | --- | --- | --- | --- |
| Component | A | B | C | D | E |
| PEG 1450 | 50.0 | — | — | — | — |
| PEG 3350 | — | 50.0 | — | — | — |
| PEG 4600 | — | — | 50.0 | — | — |
| PEG 8000 | — | — | — | 50.0 | — |
| PEG 20,000 | — | — | — | — | 50.0 |
| Simethicone (Dow Corning) | 50.0 | 50.0 | 50.0 | 50.0 | 50.0 |

The samples were prepared:
1) Weigh PEG
2) Melt and stir PEG on hot plate set at approx. 80° C. until clear.
3) Add simethicone slowly and stir at high speed for approx. 20 minutes.
4) Remove from heat and allow to cool without stirring. The resulting samples were opaque semi-solids.

EXAMPLE 2

This Example discloses semi-solid fill materials of the present invention containing 547 mg/ml simethicone. The following samples were prepared:

|  | (Amount (% w/w): | | | |
| --- | --- | --- | --- | --- |
| Component | A | B | C | D |
| PEG 400 | 0.5 | 0.5 | 0.5 | 0.5 |
| PEG 1450 | 49.5 | — | — | — |
| PEG 3350 | — | 49.5 | — | — |
| PEG 4600 | — | — | 49.5 | — |
| PEG 8000 | — | — | — | 49.5 |
| Simethicone (Dow Corning) | 50.0 | 50.0 | 50.0 | 50.0 |

The samples were prepared as follows:
1) Weigh PEGs.
2) Melt and stir PEGs on hot plate set at approx. 80°0 C. until clear.
3) Add simethicone slowly and stir at high speed for approx. 20 minutes.
4) Remove from heat and allow to cool without stirring. The resulting samples were opaque semi-solids.

EXAMPLE 3

This Example discloses semi-solid fill materials of the present invention containing 547 mg/ml simethicone. The following samples were prepared:

|  | (Amount (% w/w): | | | |
| --- | --- | --- | --- | --- |
| Component | A | B | C | D |
| PEG 400 | 3.0 | 3.0 | 3.0 | 3.0 |
| PEG 1450 | 47.0 | — | — | — |
| PEG 3350 | — | 47.0 | — | — |
| PEG 4600 | — | — | 47.0 | — |
| PEG 8000 | — | — | — | 47.0 |
| Simethicone (Dow Corning) | 50.0 | 50.0 | 50.0 | 50.0 |

The samples were prepared using the procedure of Example 2. The resulting samples were opaque semi-solids.

EXAMPLE 4

This Example discloses a semi-solid fill material of the present invention containing 547 mg/mL simethicone. The following sample was prepared:

| Component | Amount (% w/w) |
| --- | --- |
| PEG 400 | 2.5 |
| PEG 3350 | 47.5 |
| Simethicone (Dow Corning) | 50.0 |

The samples were prepared using the procedure of Example 2. The resulting sample was an opaque semi-solid.

The following summarizes the results of the sample testing of Examples 1–4 and simethicone control:

| Example | Syringeability (g) | Defoam Time (Seconds) | Viscosity (cps) |
| --- | --- | --- | --- |
| 1A | 0.047 | 11 | 3,009,000 |
| 1B | 0.091 | 5 | 1,420,566 |
| 1C | 0.180 | 9 | 331,700 |
| 1D | 0.216 | 5 | 213,420 |
| 1E | 0.300 | 8 | 9069 |
| 2A | — | — | — |
| 2B | 0.054 | 6 | 2,856,000 |
| 2C | — | — | — |
| 2D | — | — | — |
| 3A | — | — | — |
| 3B | 0.039 | 10 | 301,000 |
| 3C | — | — | — |
| 3D | 0.165 | 7 | 116,350 |
| 4 | 0.347 | 6 | 1,025,633 |
| Simethicone (Dow Corning) | 1.675 | 9 | 612 |

In the event multiple tests were conducted on the same formulation, the above data is an average of the measured values for the formulations. The semi-solids of the present invention have defoam times equal to or faster than the simethicone control. Further, the syringeability of the semi-solids of the present invention was significantly less than the simethicone control and the defoam times were less than or substantially equivalent to the simethicone control.

EXAMPLE 8

This Example discloses a soft gelatin capsule filled with a semi-solid fill material containing 547 mg/mL simethicone. The following sample was prepared:

| Component | Amount (% w/w) |
|---|---|
| PEG 400 | 2.5 |
| PEG 3350 | 47.5 |
| Simethicone (Dow Corning) | 50.0 |

The sample was prepared as follows:
1) Weigh PEGs.
2) Melt and stir on hot plate set at approx. 80° C.
3) Add simethicone slowly and stir at high speed.
4) Remove from heat and allow to cool.

The resulting formulation was an opaque semi-solid having a defoaming time of approx. 6 seconds and a viscosity of 3,000,000 cp. The semi-solid was warmed so that it would flow and then filled into hydrophobic and hydrophillic soft gelatin capsules as follows:
1) A 10 cc syringe barrel was filled with the simethicone formulation without the needle.
2) A 16 gauge needle was attached and was placed inside a pre-weighed air-filled soft gelatin capsule.
3) A 125 mg dosage of simethicone was carefully syringed into the air-filled capsule.
4) The top of the capsule was sealed with a hot iron.

The resulting soft gelatin capsules had an opaque white appearance.

Various modifications can be made to the above-described embodiments without departing from the spirit and scope of the present invention.

What is claimed is:

1. A semi-solid pharmaceutical composition, comprising:
   about 30 to about 70 percent by weight polyalkylene glycol having an average molecular weight of about 400 to about 20,000 and
   about 30 to about 70 percent by weight antiflatulent.

2. The composition of claim 1 wherein the polyalkylene glycol is polyethylene glycol.

3. The composition of claim 1 having a viscosity of about 10,000 to about 2,500,000 centipoise at 25° C.

4. The composition of claim 1 further comprising auxiliary semi-solid forming agents selected from the group consisting of propylene glycol, polyglyceryl-6-distearate, glycerol oleate and hydroxypropyl cellulose.

5. A pharmaceutical dosage form, comprising:
   a gelatin capsule shell filled with a semi-solid comprising about 30 to about 70 percent by weight polyalkylene glycol having an average molecular weight of about 400 to about 20,000 and about 30 to about 70 percent by weight antiflatulent.

6. The composition of claim 1 comprising about 0.25 to about 5 percent of a polyethylene glycol having an average molecular weight of about 600 or less and about 45 to about 50 percent of a polyethylene glycol having an average molecular weight of greater than about 600 to about 10,000, by weight of the composition.

7. The composition of claim 1 having a defoam time of less than about 15 seconds.

8. The composition of claim 1 having a syringeability of less than about 0.5 gram.

9. The composition of claim 1 wherein said antiflatulent is selected from the group consisting of simethicone and dimethicone.

10. The composition of claim 9 wherein said antiflatulent is simethicone.

11. The composition of claim 1, comprising by weight:
    about 40 to about 60 percent of polyethylene glycol having an average molecular weight of about 400 to about 3350 and
    about 40 to about 60 percent of simethicone.

12. The composition of claim 11 having a viscosity of about 400,000 to about 2,000,000 centipoise at 25° C.

13. The composition of claim 1, comprising by weight:
    about 40 to about 60 percent simethicone;
    about 1 to about 3 percent polyethylene glycol having an average molecular weight of about 300 to about 400; and
    about 40 to about 60 percent polyethylene glycol having an average molecular weight of about 1450 to about 4600.

14. The composition of claim 13 having a viscosity of about 900,000 to about 1,000,000 centipoise at 25° C., a defoam time of less than about 8 seconds and a syringeability of less than about 0.5 gram.

15. The dosage form of claim 5, comprising by weight:
    about 40 to about 60 percent simethicone;
    about 1 to about 3 percent polyethylene glycol having an average molecular weight of about 300 to about 400; and
    about 40 to about 60 percent polyethylene glycol having an average molecular weight of about 1450 to about 4600.

16. The dosage form of claim 5 wherein the polyalkylene glycol is polyethylene glycol.

17. The dosage form of claim 5 wherein said semi-solid has a viscosity of about 10,000 to about 2,500,000 at centipoise 25° C.

18. The dosage form of claim 5 wherein the semi-solid further comprises auxiliary semi-solid forming agents selected from the group consisting of propylene glycol, polyglyceryl-6-distearate, glycerol oleate and hydroxypropyl cellulose.

19. The dosage form of claim 5 wherein the shell is a soft gelatin capsule.

20. The dosage form of claim 5 comprising by weight about 0.25 to about 5 percent of a polyethylene glycol having an average molecular weight of about 600 or less and about 45 to about 50 percent of a polyethylene glycol having an average molecular weight of greater than about 600 to about 10,000.

21. The dosage form of claim 5 wherein the semi-solid has a defoam time of less than about 15 seconds.

22. The dosage form of claim 5 wherein the semi-solid has a syringeability of less than about 0.5 gram.

23. The dosage form of claim 5 wherein the antiflatulent is selected from the group consisting of simethicone and dimethicone.

24. The dosage form of claim 5 wherein antiflatulent is simethicone.

25. The dosage form of claim 24, comprising by weight:
    about 40 to about 60 percent of polyethylene glycol having an average molecular weight of about 400 to about 3350 and about 40 to about 60 percent of simethicone.

26. The dosage form of claim 25 having a viscosity of about 400,000 to about 2,000,000 centipoise at 25° C.

27. The composition of claim 15 wherein the semi-solid has a viscosity of about 900,000 to about 1,000,000 cp at 25° C., a defoam time of less than about 8 seconds and a syringeability of less than about 0.5 gram.

* * * * *